United States Patent
Wanek et al.

(10) Patent No.: US 6,919,386 B2
(45) Date of Patent: Jul. 19, 2005

(54) POLYETHER BASED PREPARATIONS AND THE USE THEREOF

(75) Inventors: Erich Wanek, Kaufering (DE); Gunther Eckhardt, Bad Duerrenburg (DE); Peter Roas, Pähl/Fischen (DE)

(73) Assignee: 3M ESPE AG, Seefeld (DE)

( * ) Notice: Subject to any disclaimer, the term of this patent is extended or adjusted under 35 U.S.C. 154(b) by 412 days.

(21) Appl. No.: 10/181,358

(22) PCT Filed: Jan. 15, 2001

(86) PCT No.: PCT/EP01/00395

§ 371 (c)(1),
(2), (4) Date: Jul. 17, 2002

(87) PCT Pub. No.: WO01/52792

PCT Pub. Date: Jul. 26, 2001

(65) Prior Publication Data

US 2003/0109596 A1 Jun. 12, 2003

(30) Foreign Application Priority Data

Jan. 17, 2000 (DE) .......................... 100 01 747

(51) Int. Cl.⁷ ............................ A61K 6/10; A61C 9/00; C08K 5/10; C08K 5/06
(52) U.S. Cl. ...................... 523/109; 524/313; 524/320; 524/505; 524/612; 528/423; 433/199.1; 433/201.1
(58) Field of Search ........................ 523/109; 524/313, 524/320, 505, 612; 528/423; 433/199.1, 201.1

(56) References Cited

U.S. PATENT DOCUMENTS

| 4,493,911 A | 1/1985 | Schmitt et al. |
|---|---|---|
| 4,532,268 A | 7/1985 | Jochum et al. |
| 5,130,348 A | 7/1992 | Zahler et al. |
| 6,127,449 A | * 10/2000 | Bissinger et al. ........... 523/109 |
| 6,383,279 B1 | 5/2002 | Eckhardt et al. |

FOREIGN PATENT DOCUMENTS

| DE | 1 745 810 | 1/1970 |
|---|---|---|
| DE | 32 46 654 A1 | 6/1984 |
| DE | 195 05 896 A1 | 8/1996 |
| DE | 197 11 514 AA | 9/1998 |
| DE | 197 40 234 A1 | 3/1999 |
| DE | 199 42 459 A1 | 3/2001 |
| EP | 0 110 429 | 6/1984 |
| EP | 0 421 371 A2 | 4/1991 |

* cited by examiner

Primary Examiner—Tae H. Yoon
(74) Attorney, Agent, or Firm—Birch, Stewart, Kolasch & Birch, LLP

(57) ABSTRACT

The invention relates to preparations, containing
(A) 30 to 56 wt.-% aziridino polyethers with a cyclic polyether content lower than 5.0 wt.-%;
(B) 30 to 45 wt.-% compounds which effect a softening of the cured dental materials;
(C) 10 to 15 wt.-% filler;
(D) 4 to 10 wt.-% further active ingredients;
with the provisos that
the weight ratio between constituents (A) and (C) to the compounds of constituent (B) is 1.2 to 2.1;
constituent (B) consists of compounds with molar masses lower than 500 g/mol (B1) and of trisacylesters of glycerol of non-animal origin with molar masses between 500 to 2000 g/mol (B2) as well as of compounds with molar masses greater than 2000 g/mol (B3) and
the weight ratio between (B1) and (B3) is 1:0.8 to 1:2.3, as well as their use.

20 Claims, No Drawings

POLYETHER BASED PREPARATIONS AND THE USE THEREOF

This application is the national phase under 35 U.S.C. §371 of PCT International Application No. PCT/EP01/00395 which has an International filing date of Jan. 15, 2001, which designated the United States of America.

The invention relates to preparations based on aziridino polyethers and their use for the preparation of dental materials, in particular impression materials.

The preparation of polyether derivatives and their use in dental materials has been known for a long time. Thus DE-C-174 58 10 for example describes the preparation of shaped bodies based on aziridino polyethers.

In the documents DE-C-32 46 654, EP-A-0 421 371 and EP-A-0 110 429 the use of aziridino polyethers in polyether impression materials is described.

The modelling of the actual conditions in the patient's mouth using suitable impression materials is the prerequisite for the preparation of precisely fitting prostheses, crowns and bridges, inlays and onlays.

Materials based on aziridino polyethers differ from the known impression materials through their hydrophilic character, which makes possible a very high precision of the impressions.

A disadvantage with these materials is however that they cannot be very easily demoulded. This means that the demouldability of the impression when modelling and the demouldability of the plaster model after the casting of the impression are not satisfactory.

In DE-A-197 40 234 dental materials are described which are based on polyether derivatives and characterized in that their cyclic oligomeric polyether content is lower than 5.0%. It is stated that the cyclic polyether oligomers present in the polyether materials are responsible for the poor demouldability of the impression when modelling as well as a poor demouldability of the plaster model after the casting of the impression.

The object of the present invention is to prepare dental materials which are based on aziridino polyethers which are characterized by an easier demouldability.

This object is achieved by preparations and dental materials prepared from them, as they are described in the claims.

It was found that the removability of the impression and the demouldability of the plaster model while maintaining the high impression precision can also be further improved in the case of aziridino polyether-based impression materials with a reduced cyclic polyether content if low hardness values of the set elastomer materials are adjusted by the selection of the active ingredients and the concentration ratios of the active ingredient groups in the impression preparation admixed from the catalyst component and the base component.

It was surprising, and not foreseeable, that clearly lower hardness values can be achieved with roughly the same consistency of the admixed impression preparations compared with the previously described impression materials based on aziridino polyethers and that the flow-on behaviour of the impression preparations according to the invention are clearly improved vis-à-vis the impression materials according to the state of the art, which results in a higher design sharpness.

Complicated clinical situations, such as the modelling of subgingival preparation limits in the presence of blood and saliva, can thus also be handled better.

Polyether-based dental materials within the meaning of this invention preferably have Shore A hardness values in the range from 45 to 55.

The dental materials formulated from the preparations according to the invention include in particular two components, namely the catalyst component and the base component.

The catalyst component contains at least one starter substance and the base component the aziridino polyethers.

The individual active ingredients or active ingredient groups which are suitable for achieving a good processability and for acquiring the desired combination of properties of the cured elastomers can be contained proportionally in the catalyst component and the base component or in only one of the components.

The distribution of these active ingredients among the components depends on the sought mixing ratio, ease of miscibility and the sufficient storage stability of the resultant substance mixtures in the separately stored components.

This distribution can be optimised by corresponding series of tests.

The achievable properties during modelling and in the cured impression materials depend predominantly on the mixing quality and the overall composition of the impression preparation.

An adequate mixing quality is achieved with manual admixing for example by intensive spatula-mixing onto a mixing block until a uniform coloring of the mixture from the differently coloured components is achieved.

The practical implementation of the mixing process by means of continuous mixers is advantageous, in most cases consisting of a volume-dosing unit and static or dynamic mixing elements.

With these devices an adequate mixing quality can be achieved, which can be easily monitored by means of the uniform coloring.

Normally in the case of polyether-based dental materials, the volume mixing ratio between catalyst component and base component is set at values from 1:1 to 1:10, the settings 1:2 and 1:5 being particularly preferred.

The polyether-based dental materials according to the invention with improved demouldability and improved flow-on behaviour are obtained from preparations, containing:

(A) 30 to 56 wt.-%, preferably 41 to 54 wt.-% of aziridino polyethers with a cyclic polyether content lower than 5.0 wt.-% and preferably lower than 0.9 wt.-%;

(B) 30 to 45 wt.-%, preferably 30 to 42 wt.-% of compounds which effect a softening of the cured dental materials;

(C) 10 to 15 wt.-%, preferably 12 to 14 wt.-% fillers;

(D) 4 to 10 wt.-%, preferably 4 to 7 wt.-% of further active ingredients, such as colouring agents, aromatics, starters, retarders, accelerators and surfactants;

with the provisos that the weight ratio between constituents (A) and (C) to the compounds of constituent (B) is 1.2 to 2.1, preferably 1.3 to 1.9, constituent (B) consists of compounds with molar masses lower than 500 g/mol (B1) and of trisacyl esters of glycerols of non-animal origin with molar masses between 500 to 2000 g/mol (B2) as well as of compounds with molar masses greater than 2000 g/mol (B3) and the weight ratio between (B1) and (B3) is 1:0.8 to 1:2.3.

The aziridino polyethers used according to constituent (A) can be prepared from polyether polyols which are preferably prepared by copolymerisation of tetrahydrofuran and ethylene oxide in the molar ratio 10:1 to 1:1, preferably 5:1 to 3:1 in the presence of strong acid, such as for example boron fluoride etherates.

It is likewise possible to use polyether polyols which in addition to tetrahydrofuran units also contain ethylene oxide units and or propylene oxide units.

The polyether polyols possess at least 2 hydroxyl groups but can also contain up to 20 hydroxyl groups per molecule.

The molar masses ($M_n$) of the polyether polyols used for functionalization are normally in the range of 500 to 20000 g/mol, preferably in the range of 2000 to 10000 g/mol. The functionalization with aziridino groups can for example take place according to the process described in DE-C-1 745 810.

For the preparation of the soft dental materials according to the invention, bis-aziridino polyethers with aziridino equivalent masses of 2000 to 4000 g/equivalent are preferably used as constituent (A), the polyether part consisting of oxytetramethylene and oxydimethylene units preferably in the ratio of 4:1 to 3:1 and the proportion of oligomeric cyclic ethers in the bis-aziridino polyethers being lower than 0.5 wt.-%, preferably lower than 0.3 wt.-%.

The cyclic oligomeric polyethers can be removed both during the process step of the polyether polyols and after their functionalization with aziridino groups, distillative and extractive processes or membrane separation being applicable.

A typical process for the preparation of an aziridino polyether which has been largely freed of oligomeric cyclic ethers is described in preparation example 2 of DE-A-197 40 234.

In order to achieve the desired properties the impression materials contain 30 to 45 wt.-% of compounds which effect a softening of the cured dental materials.

Such compounds can be both typical plasticizers as also supplied for other polymeric systems, such as esters of polyvalent carboxylic acids, polyaromatic compounds and sulfonic acid esters or compounds which, in addition to the softening, also bring about other effects such as for example surfactant effect, an increase in standing stability and an improvement in the flow behaviour.

It was surprisingly found that the desired properties of soft polyether-based dental materials, starting from aziridino polyethers with a greatly reduced oligomeric cyclic polyether content, can be achieved in particular if special compound classes of these compounds effecting the softening are used and a specific ratio of these compounds classes relative to each other is maintained.

Thus, the preparations according to the invention according to constituent (B) contain three compound classes of compounds which effect a softening of the cured dental materials, namely (B1) typical plasticizers with molar masses lower than 500 g/mol, (B2) trisacyl glycerides solid at room temperature with molar masses in the range from 500 to 2000 g/mol, (B3) polymers liquid at room temperature with molar masses above 2000 g/mol, the weight ratio between (B1) and (B3) being 1:0.8 to 1:2.3. Various types of plasticizers are used as compounds according to portion (B1), including typical plasticizers of the ester type, such as:

$C_{12}$ to $C_{15}$ alkyl lactates, ethyl or butyl esters of citric acid or of acetyl citric acid, phthalic acid esters of longer branched alcohols, such as bis(2-ethylhexyl)-phthalate or phthalic acid polyester, $C_2$ to $C_{18}$ dialkyl esters of $C_2$ to $C_6$ dicarboxylic acids, such as bis(2-ethylhexyl)-adipate, dioctyl malate, diisopropyl adipate, aromatic and aliphatic sulfonic acid esters, such as $C_2$ to $C_{20}$ alkyl sulfonic esters of phenol or of $C_1$ to $C_{18}$ alkanols and typical aromatic plasticizers, such as:

polyphenyls in a wide viscosity range, including waxy polyphenyls (Monsanto), dibenzyl toluene, isomer mixtures of $C_{20}$ to $C_{30}$ aromatics, the use of mixtures of plasticizers of the ester type and the aromatic type being preferred.

An example of a preferred mixture is acetyltributyl citrate and dibenzyl toluene, According to constituent (B2) trisacyl esters of glycerol of non-animal origin are used.

Constituent (B2) can consist of modified fats of plant origin, such as for example of hydrogenated palm oil or soya oil or of synthetic fats.

Suitable fats are described in DE-A-197 11 514, to the entire contents of which reference is made here. Particularly suitable are avocado oil, cottonseed oil, groundnut oil, cocoa butter, pumpkin seed oil, linseed oil, maize germ oil, olive oil, palm oil, rice oil, rapeseed oil, safflower oil, sesame oil, soya oil, sunflower oil, grapeseed oil, wheatgerm oil, borneo tallow, fulwa tallow, hemp oil, illipe butter, lupin oil, candlenut oil, kapok oil, katiau fat, kenaf seed oil, kekuna oil, poppy oil, mowrah butter, okra oil, perilla oil, sal butter, shea butter and tung oil, so long as these fats were cured before their use. Fats considered suitably hardened are those whose iodine number (measured according to standard DGF C-V 11b) is lower than 20. Fats are particularly preferred whose iodine number is lower than 5. The carrying out of fat hardening is described for example in "Ullmanns Enzyklopädie der industriellen Chemie [Ullmann's Encylopaedia of Industrial Chemistry]", $4^{th}$ Edition, Volume 11, p 469. Mixtures of these naturally occurring fats can likewise be used as well as synthetically prepared fats, such as Softisan 154 or Dynasan 118 (Hüls). The preparation of such synthetic triacyl glycerides is relatively simple for the person skilled in the art and can be carried out, for example, from glycerol and the corresponding fatty acid methyl esters. Such esterification reactions are described, inter alia, in "Houben-Weyl, Methoden der Organischen Chemie [Methods of Organic Chemistry]", Vol. E5/Part 1, p. 659 ff. Preferred triacyl glycerides correspond to the formula:

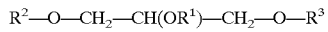

in which $R^1$, $R^2$ and $R^3$ independently of each other represent $C_{11}H_{23}CO$, $C_{13}H_{27}CO$, $C_{15}H_{31}CO$ or $C_{17}H_{35}CO$. Mixtures of such triacyl glycerides can also be considered.

According to constituent (B2) of the present invention synthetic fats with a steaoryl content of more than 65 wt.-% of the triglyceride are preferably used.

A particular effect results from the liquid polymer compounds in the preparations according to the invention. These compounds with molar masses over 2000 g/mol can belong to various compound types, such as polyether type, polyester type, polyurethane type, polycarbonate type, polyolefin type, preference being given to hydroxyl, ether, alkyl and acyl groups as end groups.

The end groups and where appropriate further functional groups are preferably selected such that no undesired reactions occur during storage of the two components and after mixing.

Particularly preferred end groups are the primary and the secondary OH group as well as the acetyl group.

A special compound class of liquid polymers are those of the polyether type.

Polyethers which possess the same or a similar molar mass as the aziridino polyethers used in constituent (A) stand out in particular.

Bis-hydroxyl or bis-acetyl-polyethers of oxytetramethylene and oxydimethylene units in the ratio 4:1 to 3:1 and molar masses in the range of 3000 to 8000 g/mol and an oligomeric cyclic ether content lower than 0.5 wt.-% are particularly preferred.

Polypropylene oxide polyols and/or copolymerisates and/or block copolymerisates of ethylene oxide and propylene oxide with hydroxyl or acetyl end groups can also be used in the mixture with these special polyethers or else as single compounds according to constituent (B3).

With the block copolymerisates with molar masses greater than 2000 g/mol the solubilizing effect of these surfactant-like compounds can additionally be used.

Furthermore the flow behaviour and the necessary setting of hydrophilia and hydrophobia of the mixed preparations can be decisively influenced by the choice and the mixture of the previously mentioned polyether derivatives.

The preparations according to the invention contain as constituent (C) 10 to 15 wt.-% of strengthening fillers.

For this purpose, organic and inorganic solids can be used which give rise to no undesired reactions in the substance mixtures of the respective component during the necessary storage and do not adversely effect the setting process after the mixing of the separately stored components.

Fillers containing more than 90 wt.-% $SiO_2$, such as quartz powder and finely dispersed silicic acids of synthetic or natural origin, have proven particularly successful.

Pyrogenic silicic acids and precipitation silicic acids which are used mostly in surface-modified form are preferred as is diatomaceous earth from various locations.

Mixtures of treated diatomaceous earth with a pH value of the 5% aqueous suspension from 8 to 10 and pyrogenic, surface-modified silicic acid with BET surfaces of 100 to 300 $m^2/g$ are particularly preferred fillers according to constituent (C).

Furthermore the preparations according to the invention according to constituent (D) contain 4 to 10 wt.-% of further active ingredients such as dyes and dye pigments, aromas and taste adjusters, starter substances such as for example sulfonium salts or acids, aminic or alkaline retarders, accelerator compounds and further non-polymeric surfactants.

The preparations according to the invention can be used in very different dental materials used in dentistry or dental engineering. Preferred application fields of such dental materials are the single-phase and the two-phase dental modelling and bite registration.

A further subject of the invention are packages and mixing devices containing materials produced from the preparations according to the invention, in particular dental materials, such as cartridges, bags, dental trays, static and dynamic mixers or mixing apparatuses.

The invention is explained further using the following examples, without being limited to these.

EXAMPLES

Preparation Examples of Base and Catalyst Pastes

A bis-aziridino polyether with a low cyclic oligomeric polyether content starting from a bis-aziridino polyether which was obtained according to DE-C-174 58 10, is prepared according to preparation example 2 of DE-A-197 40 234.

The residual cyclic oligomeric polyether content in these aziridino polyethers is determined by gas chromatography, using the method described in DE-A-197 40 234.

The base components characterized in Table 1 are prepared on a laboratory kneader to 500-g scale from this bis-azirdino polyether with a numerically average molar mass of 6100 g/mol and an ethylene oxide to tetrahydrofuran units incorporation ratio of 1:3.6 as well as a residual oligomeric cyclic polyether content of 0.25 wt.-%.

The catalyst pastes characterized in Table 2 are prepared in a laboratory kneader to 100-g scale.

In order to establish the properties named in Tables 4 and 5 the components according to the examples in Table 3 are mixed on the block.

Preparation of Impressions

The catalyst components and the base components were mixed in the stated ratio on the mixing block, the mixtures transferred to a metal tray and the filled dental tray introduced into the test subject's mouth.

In the examples 1, 2, 3, 5, 6, 7 according to the invention and in the comparison examples 1 and 2 the dental tray was filled exclusively with the admixed material (monophase technique).

In example 4 according to the invention the dental tray was filled with the material of example 3 according to the invention, but the material of example 4 according to the invention was sprayed round the test subject's teeth (double-mixing technique).

In comparison example 3, the dental tray was filled with the material of comparison example 1, but the material of comparison example 3 was sprayed round the test subject's teeth (double-mixing technique).

After a setting time of 6 minutes, calculated from the beginning of the mixing, the impressions were removed.

The removability of the impression from the test subject's mouth was evaluated by two operators according to the procedure described in DE-A-197 40 234, in each case on eight test subjects with different dental situations, and the average of the subjective impressions determined.

The following evaluation scale was used for the removability from the mouth:

1 (very good), 2 (good), 3 (satisfactory), 4 (unsatisfactory), 5 (poor).

Following the evaluation of removability, the flow-on behaviour of the admixed impression preparation was evaluated in the impression by observing the sulcus reproduction including the preparation limit and assessment of the details of the surface structure.

| Evaluation Criteria | |
| --- | --- |
| 1 | Sulcus and preparation limit are reproduced absolutely error-free and with a fine end flow. Perfect reproduction of the surface details of the hard tooth substance (preparation furrows, marginal gap in the case of fillings, transition zones). Mucous membrane profile is precisely represented. |
| 2 | Sulcus and preparation limit are well reproduced. Good reproduction of the surface details of the hard tooth substance (preparation furrows not completely dissolved, marginal gaps easily recognisable). |
| 3 | Sulcus and preparation limit are not continuously reproduced. |

Determination of the Demouldability of the Impression from the Plaster Model Demouldability was determined using a specially prepared plastic model of the lower jaw.

In the case of this plastic model of the lower jaw the 6 front teeth (dental classification=43, 42, 41, 31, 32, 33) were prepared such that there was a very marked loss of substance in the case of the prepared teeth 41 and 31.

Furthermore the premolar 45 was provided with strong undercuts and was included in the evaluation as an example of a stand-alone tooth which had suffered a marked reduction in substance as a result of periodontal damage.

The plastic model was moulded with the given impression preparations and the impressions thus obtained were cast with a stone plaster after a setting time of one hour.

After a plaster curing time of 24 hours the impression was removed from the mould and evaluated.

| Evaluation Criteria | |
|---|---|
| 1 | The plaster model was able to be demoulded quickly and without great exertion of force and displayed no damage (fractures) |
| 2 | The plaster model displayed no damage. |
| 3 | Only the two teeth which had suffered a marked reduction in substance and were therefore at risk of fracture (41 and 31) are damaged (fractured) upon demoulding. |
| 4 | More than three of the prepared teeth (43, 42, 41, 31, 32, 33) are damaged upon demoulding (fracture damage). |
| 5 | The prepared teeth (43, 42, 41, 31, 32, 33) are damaged upon demoulding (fracture damage) and the stand-alone premolar (45) breaks away from the plaster model. |

Demouldability was determined in each case by three people. The average of the three individual values was determined.

The preparations of the examples of the invention as regards the curing impression preparations correspond in all points to the criteria and conditions according to the invention, while the comparison examples do not fulfil these criteria and conditions in at least one point.

The Shore A hardness values of the examples of the invention are in the desired range for soft impression materials (Shore A: 45 to 55, measured according to DIN 53505).

The advantages of removability from the mouth and demouldability of the plaster model which are achieved with the preparations of examples 1 to 7 according to the invention can be seen in Table 4.

The advantages in the flow-on behaviour of the admixed impression preparations (design sharpness) can be seen in Table 5.

TABLE 1

Preparation of the base components

| Constituent | Base components according to the invention | | | | | | | Comparison | |
|---|---|---|---|---|---|---|---|---|---|
| | B1 | B2 | B3 | B4 | B5 | B6 | B7 | VB1 | VB2 |
| (A) | | | | | | | | | |
| Bis-aziridino polyether, $M_n$ = 6100 g/mol, ethylene oxide to tetrahydrofuran units incorporation ratio of 1:3.5, residual oligomeric cyclic polyether content of 0.25 wt.-% | 54.7 | 51.6 | 60.1 | 79.9 | 54.5 | 53.0 | 54.0 | — | 57.8 |
| (B1) | | | | | | | | | |
| Dibenzyl toluene | 7.9 | 0.2 | 13.1 | 7.1 | | 15.1 | 5.0 | 11.2 | 11.2 |
| $C_{20}$ to $C_{25-}$ aromatics mixture | | | | | 4.1 | | | | |
| Acetyltributyl citrate | | | | 0.9 | | | | | |
| (B2) | | | | | | | | | |
| Synthetic fat with a stearoyl portion of 75 wt.-% | 15.3 | 18.9 | 9.6 | 5.0 | | 15.0 | | | |
| Hydrogenated palm oil | | | | | 17.1 | | 17.7 | | |
| (B3) | | | | | | | | | |
| Bisacetyl polyether, $M_n$ = 5950 g/mol, ethylene oxide to tetrahydrofuran units incorporation ratio of 1:3.6; residual oligomeric cyclic polyether content of 0.29 wt.-% | 15.0 | 21.3 | 7.0 | 1.6 | — | — | 6.2 | | |
| Polypropylene diol with a molar mass of 2000 g/mol | | | | | 15.0 | 7.6 | | | |
| Block copolymer comprising a polypropylene oxide centre block and ethylene oxide end blocks and a molar mass of 6500 g/mol | — | — | 0.2 | 0.4 | | | 7.0 | | |
| (C) Diatomaceous earth, pH value of the 5% aqueous dispersion: 9.4 | 4.9 | 6.0 | 7.6 | 2.0 | 6.5 | 7.0 | 7.6 | 13.9 | 13.9 |
| (D) | | | | | | | | | |
| Aromas | 0.1 | 0.3 | 0.3 | 0.3 | 0.3 | 0.3 | 0.2 | | |
| Lauryl imidazole | 0.5 | 0.3 | 0.7 | 0.7 | 0.7 | 0.3 | 0.5 | | |
| Coloring paste, grey | 1.6 | 1.4 | 1.4 | 2.1 | 1.8 | 1.7 | 1.8 | 2.6 | 2.6 |
| (—) | | | | | | | | | |
| Aziridino polyether, prepared according to DE-C-1 745 810, $M_n$ = 6100 g/mol ethylene oxide to tetrahydrofuran units incorporation ratio of 1:3.6; containing 8.2 wt.-% of cyclic oligomers | | | | | | | | 57.8 | — |
| Hydrogenated beef tallow | | | | | | | | 14.5 | 14.5 |

TABLE 2

Preparation of the catalyst components

| Constituent | Catalyst components according to the invention K1 | K2 | Comparison VK1 |
|---|---|---|---|
| (B1) | | | |
| Acetyltributyl citrate | 39.9 | 18.9 | 32.0 |
| Dibenzyl toluene | | 5.5 | |
| (B2) | | | |
| Synthetic fat with a steaoryl portion of 75 wt.-% | — | 2.0 | |
| (B3) | | | |
| Bisacetylpolyether, $M_n$ = 5950, ethylene oxide to tetrahydrofuran units incorporation ratio of 1:3.6; residual oligomeric cyclic polyether content of 0.29 wt.-% | 0.5 | 28.9 | |
| Block copolymer comprising a polypropylene oxide centre block and polyethylene oxide end blocks and a molar mass of 6500 g/mol | 3.5 | 2.7 | 5.8 |
| (C) | | | |
| Diatomaceous earth | 12.1 | 23.0 | 9.5 |
| Pyrogenic silicic acid, hydrophobically modified, BET-surface 160 m²/g | 24.1 | 5.3 | 19.1 |
| (D) | | | |
| Sulfonium starter according to Example 27 of DE-A-2 515 593 | 19.3 | 13.4 | 32.9 |
| Coloring paste, red | 0.6 | 0.3 | 0.7 |

TABLE 3

Characterization of the preparation of the curing impression preparations

| | Examples according to the invention | | | | | | | Comparison examples | | |
|---|---|---|---|---|---|---|---|---|---|---|
| | 1 | 2 | 3 | 4 | 5 | 6 | 7 | 1 | 2 | 3 |
| Base component according to Table 1 | B3 | B2 | B1 | B4 | B5 | B6 | B7 | VB1 | VB2 | VB1 |
| Catalyst component according to Table 2 | K1 | K1 | K1 | K2 | K1 | K1 | K1 | K1 | K1 | VK1 |
| Mixing ratio by weight Catalyst component: base component | 1:4.2 | 1:4.1 | 1:4.2 | 1:1.7 | 1:5.0 | 1:4.9 | 1:4.8 | 1:4.2 | 1:4.1 | 1:5.6 |

TABLE 4

Evaluation of demouldability

| | Removability from the mouth (Average values) | Demouldability of the plaster model (Average values) |
|---|---|---|
| Example according to the invention | | |
| 1 | 1.6 | 1.7 |
| 2 | 1.3 | 1.3 |
| 3 | 1.4 | 1.3 |
| 4 | 1.5 | 1.7 |
| 5 | 1.6 | 1.7 |
| 6 | 1.4 | 1.7 |
| 7 | 1.7 | 2.0 |
| Comparison example | | |
| 1 | 4.3 | 3.7 |
| 2 | 4.8 | 4.2 |
| 3 | 2.7 | 2.7 |

TABLE 5

Characterization of the cured dental materials and the flow behaviour

| Property | Examples according to the invention | | | | | | | Comparison Examples | | |
|---|---|---|---|---|---|---|---|---|---|---|
| | 1 | 2 | 3 | 4 | 5 | 6 | 7 | 1 | 2 | 3 |
| Shore A hardness, DIN 53505 (measured after 24 hours) | 54 | 47 | 50 | 53 | 52 | 52 | 55 | 60 | 64 | 58 |
| Tensile strength (MPa), internal standard | 1.5 | 1.1 | 1.3 | 1.0 | 1.7 | 1.5 | 1.6 | 1.5 | 1.8 | 1.5 |
| Elongation at break (%), internal standard | 140 | 130 | 130 | 95 | 190 | 143 | 158 | 94 | 107 | 150 |
| Consistency according to EN 24823 (in mm disk diameter) | 37 | 32 | 35 | 42.5 | 35 | 38 | 31 | 36 | 34 | 35 |
| Gap-flow properties ("Shark's fin test") in mm flow path | 26 | 16 | 27 | 26 | 21 | 27 | 14 | 20 | 16 | 17 |
| Accuracy of reproduction (evaluation, average values) | 1.1 | n.a. | 1.3 | 1.0 | 1.3 | 1.1 | n.a. | 2.1 | 2.4 | 2.4 | n.a. = not applicable (tray materials)

What is claimed is:

1. A preparation comprising:
   (A) 30 to 56 wt.-% aziridino polyethers with a cyclic polyether content lower than 5.0 wt.-%;
   (B) 30 to 45 wt.-% compounds which effect a softening of the cured dental materials;
   (C) 10 to 15 wt.-% fillers;
   (D) 4 to 10 wt.-% further active ingredients;
   with the provisos that
   the weight ratio between constituents (A) and (C) to the compounds of constituent (B) is 1.2 to 2.1;
   constituent (B) comprises (B1) compounds with molar masses lower than 500 g/mol, (B2) trisacyl esters of glycerol of non-animal origin with molar masses between 500 to 2000 g/mol and (B3) compounds with molar masses greater than 2000 g/mol; and
   the weight ratio between (B1) and (B3) is 1:0.8 to 1:2.3.

2. The preparation according to claim 1, in which bis-aziridino polyethers with aziridino equivalent masses of 2000 to 4000 g/equivalent are used as constituent (A), the polyether part consists of oxytetramethylene and oxydimethylene units in the ratio 4:1 to 3:1 and the proportion of oligomeric cyclic ethers in the bis-aziridino polyethers is lower than 0.5 wt.-%.

3. The preparation according to claim 1, in which constituent (B1) comprises at least one ester plasticizer or at least one aromatic plasticizer or a mixture of at least one ester plasticizer and at least one aromatic plasticizer.

4. The preparation according to claim 1, in which the trisacyl esters of glycerol of constituent (B2) are synthetic fats with a steaoryl content of more than 65 wt.-% of the triglyceride.

5. The preparation according to claim 1, in which constituent (B3) is at least one liquid polymer selected from the group consisting of a polyether polymer, a polyester polymer, a polyurethane polymer, a polycarbonate polymer and a polyolefin polymer.

6. The preparation according to claim 5, in which the component (B3) is at least one liquid polyether polymer having the same or a similar preparation and molar mass as the aziridino polyethers used as constituent (A), but bearing hydroxyl or acetyl end groups.

7. Preparation according to claim 5, in which the component (B3) is at least one liquid polyether polymer that is a polypropylene oxide polyol.

8. The preparation according to claim 5, in which the component (B3) is at least one liquid polyether polymer that is a statistical copolymerizate or block copolymerizate of ethylene oxide and propylene oxide with hydroxyl or acetyl end groups.

9. The preparation according to claim 1, in which mixtures of finely dispersed silicic acids of natural and synthetic origin are used as constituent (C).

10. A package containing at least one dental material that is produced from a preparation according to claim 1.

11. A mixing device containing at least one dental material that is produced from a preparation according to claim 1.

12. The preparation of claim 3, in which the ester plasticizer is selected from the group consisting of ethyl esters of citric acid, butyl esters of citric acid, ethyl esters of acetyl citric acid, butyl esters of acetyl citric acid, phthalic acid esters of longer branched alcohols, dialkyl esters of dicarboxylic acids, aromatic sulfonic acid esters and aliphatic sulfonic acid esters.

13. The preparation of claim 12, in which the at least one ester plasticizer is bis(2-ethylhexyl)-adipate, an alkylsulfonic acid ester of phenol or an alkylsulfonic ester of an alkanol.

14. The preparation of claim 3, in which the aromatic plasticizer is selected from the group consisting of a polyphenyl, dibenzyl toluene, and an isomer mixture of a $C_{20}$ to $C_{30}$ aromatic compound.

15. The preparation of claim 3, in which the at least one plasticizer is a mixture of ester and aromatic plasticizers.

16. The preparation of claim 5, in which the polymer has hydroxyl, ether, alkyl and/or acyl groups as end groups.

17. The preparation of claim 9, in which component (C) is diatomaceous earth or at least one pyrogenic, surface-modified silicic acid with a BET surface area of 100 to 300 $m^2/g$.

18. The preparation of claim 1, having a Shore A hardness value ranging from 45 to 55.

19. A method for making a dental model, comprising applying the preparation of claim 1 to the mouth of a patient to form an impression, and
   curing the preparation to form a dental model.

20. A method for preparing a dental composition comprising providing components
   (A) 30 to 56 wt.-% aziridino polyethers with a cyclic polyether content lower than 5.0 wt.-%;

(B) 30 to 45 wt.-% compounds which effect a softening of the cured dental materials;

(C) 10 to 15 wt.-% fillers;

(D) 4 to 10 wt.-% further active ingredients;

the components (A) and (C) being provided in a weight ratio to component (B) of from 1.2 to 2.1;

constituent (B) comprising (B2) compounds with molar masses lower than 500 g/mol, (B2) trisacyl esters of glycerol of non-animal origin with molar masses between 500 to 2000 g/mol and (B3) compounds with molar masses greater than 2000 g/mol, the weight ratio between (B1) and (B3) being 1:0.8 to 1:2.3; and mixing the components (A), (B), (C) and (D).

* * * * *

UNITED STATES PATENT AND TRADEMARK OFFICE
CERTIFICATE OF CORRECTION

PATENT NO. : 6,919,386 B2  
APPLICATION NO. : 10/181358  
DATED : July 19, 2005  
INVENTOR(S) : Erich Wanek Page 1 of 1

It is certified that error appears in the above-identified patent and that said Letters Patent is hereby corrected as shown below:

Column 4
Line 12, after "dibenzyl" delete "toluene," and insert -- toluene. -- therefor.

Column 14
Line 1, in claim 20, after "comprising" delete "(B2)" and insert -- (B1) -- therefor.

Signed and Sealed this

Thirteenth Day of May, 2008

JON W. DUDAS
*Director of the United States Patent and Trademark Office*